United States Patent [19]

Landscheidt et al.

[11] Patent Number: 5,302,742

[45] Date of Patent: Apr. 12, 1994

[54] PROCESS FOR THE PREPARATION OF N-ACYLATED P-AMINO-PHENOLS

[75] Inventors: Heinz Landscheidt, Duisburg; Alexander Klausener, Cologne; Heinz-Ulrich Blank, Odenthal-Gloebusch, all of Fed. Rep. of Germany

[73] Assignee: Bayer Aktiengesellschaft, Leverkusen, Fed. Rep. of Germany

[21] Appl. No.: 58,549

[22] Filed: May 5, 1993

[30] Foreign Application Priority Data

May 12, 1992 [DE] Fed. Rep. of Germany ....... 4215592

[51] Int. Cl.$^5$ .......................................... C07C 269/00
[52] U.S. Cl. ........................................ 560/29; 560/30; 560/31; 560/32; 564/161; 564/169; 564/192
[58] Field of Search ............... 560/29, 30, 31, 32; 564/161, 169, 192

[56] References Cited

U.S. PATENT DOCUMENTS 2,998,450  8/1961  Wilbert et al. ............... 564/141
3,917,695  11/1975  Schulman et al. ............ 564/144
5,059,623  10/1991  Kruger et al. ................ 514/613

FOREIGN PATENT DOCUMENTS 0339418  11/1989  European Pat. Off. .

OTHER PUBLICATIONS

Methoden Der Organischen Chemie, (Houben–Weyl) Bd. VI/1C, 1976, Stuttgard, pp. 91–101.

*Primary Examiner*—José G. Dees
*Assistant Examiner*—Joseph M. Conrad
*Attorney, Agent, or Firm*—Sprung Horn Kramer & Woods

[57] ABSTRACT

N-acylated p-amino-phenols can be prepared by catalytical hydrogenation of the underlying aromatic nitro compounds in a reaction medium of aqueous sulfuric acid in the sense of a Bamberger type reaction at elevated temperature, optionally in the presence of a water-miscible organic solvent, and subsequent reaction of this reaction mixture with an acid chloride, optionally in the presence of an acid binder and optionally in the presence of a diluent.

20 Claims, No Drawings

PROCESS FOR THE PREPARATION OF N-ACYLATED P-AMINO-PHENOLS

BACKGROUND OF THE INVENTION

1. Field of the Invention

The invention relates to a process for the preparation of N-acylated p-amino phenols by catalytic hydrogenation or aromatic nitro compound having a free p position in accordance with a Bamberger reaction and subsequent acylation of the resulting amino group.

N-acylated p-amino-phenols are known as pest control agents, in particular as fungicides (EP 339 418).

2. Description of the Related Art

The preparation of N-acylated p-amino-phenols is conventionally carried out by acylation of the corresponding free p-amino-phenols in the presence of diluents and with the aid of basic auxiliaries (EP 339 418). The p-amino-phenols required are compounds known in principle and are generally prepared by nitration of p-unsubstituted hyroxyaromatic compounds and subsequent reduction of the nitro group or by reduction of p-unsubstituted nitro-aromatic compounds in accordance with a Bamberger reaction (Houben-Weyl, 4th edition, Volume VI/1c; (1976), pp. 85-117). In both cases it is conventional and necessary to isolated the free p-amino-phenols required as intermediates for the preparation of the desired N-acylated p-amino-phenols and to react them further in purified form. This procedure is complex, uneconomic and associated with losses in yield and high production of wastes, in particular effluents. Moreover, the nitration of phenols gives cause for concern with respect to reaction and safety aspects.

SUMMARY OF THE INVENTION

The object was therefore to find a process for the preparation of the abovementioned N-acylated p-amino-phenols which avoids multi-step and complicated reaction sequences, avoids the nitration of hydroxyaromatic compounds and which leads to products of high purity in good yields.

This object is achieved by the process according to the invention without intermediate isolation of the p-amino-phenol.

The present invention relates to a process for the preparation of N-acylated p-amino-phenols of the general formula

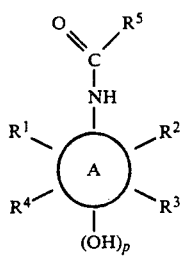

(I)

in which

A represents a benzene or naphthalene nucleus,
p indicates the p position to the amino group,
$R^1$, $R^2$, $R^3$ and $R^4$, independently of each other, denote hydrogen, $C_1$-$C_4$-alkyl, $C_1$-$C_4$-alkoxy, halogen or the group CO—$R^6$ in which $R^6$ represents hydrogen, $C_1$-$C_4$-alkyl, $C_1$-$C_4$-alkoxy, hydroxyl or unsubstituted or substituted aryl, and $R^5$ denotes $C_1$-$C_{20}$-alkyl, $C_3$-$C_{10}$-cycloalkyl, $C_5$-$C_{10}$-cycloalkenyl, $C_1$-$C_{10}$-alkoxy, unsubstituted or substituted aryloxy or unsubstituted or substituted aryl, which is characterised in that nitro compounds of the general formula $$\begin{array}{c} NO_2 \\ R^1 \diagdown \bigcirc \diagup R^2 \\ A \\ R^4 \diagup \bigcirc \diagdown R^3 \\ (H)_p \end{array} \quad (II)$$

in which $R^1$ to $R^4$, A and p have the above meanings, are hydrogenated in an aqueous acidic reaction medium in which the amount of water is 2 to 40 times, preferably 3 to 30 times, particularly preferably 4 to 20 times, the amount by weight of the aromatic nitro compound, and in the absence or presence of a water-miscible organic solvent with the aid of a catalyst selected from the group comprising the platinum metals in accordance with a Bamberger reaction at a temperature of 50°-160° C., preferably 70°-140° C., particularly preferably 90°-120° C. and a hydrogen partial pressure of 0.1-50 bar, preferably 0.5-30 bar, particularly preferably 1-20 bar and the resulting reaction mixture is reacted with a compound of the formula $$R^5-C\diagup_X^{\diagdown O} \quad (III)$$

where $R^5$ has the above iteanina and
X represents a leaving group,
in an amount of 0.5-2 mol, preferably 0.8-1.4 mol, per mol of the nitro compound used, at a temperature of −30° C. to +150° C., preferably −20° C. to +120° C., particularly preferably −10° C. to +100° C., and in the absence or presence of a basic auxiliary or another acid acceptor and in the absence or presence of a diluent.

DETAILED DESCRIPTION OF THE INVENTION

It is a surprising advantage of the process according to the invention that the reaction mixture obtained in the catalytic hydrogenation of p-unsubstituted nitroaromatic compounds under aqueous acidic conditions in accordance with a Bamberger reaction can he reacted smoothly with acylation agents of the general formula (III), the desired products of the general formula (I) being obtained without the losses in yields, caused by hydrolysis of the abovementioned acylation agents of the formula (III), being observed.

A further surprising advantage of the process according to the invention is that the desired products of the general formula (I) are obtained in high purities although isolation and intermediate purification of the p-amino-phenols occurring as intermediates, as in the prior art, is dispensed with.

Further advantages are:
the reduction of effluent pollution compared with the previous process the increase of the economic efficiency by reduction of the number of the required process steps.

$C_1$–$C_4$-alkyl is, for example, methyl, ethyl, propyl, 2-propyl, butyl, 2-butyl, 2-methyl-propyl (isobutyl), 2-methyl-2-propyl (tert-butyl); a further alkyl having up to 20 C atoms is, for example, pentyl, 2-pentyl, 3-pentyl, 2,2-dimethyl-propyl (neopentyl), 2-methyl-2-butyl, 3-methyl-2-butyl, hexyl, 2-hexyl, 3-methyl-3-pentyl, 3,3-dimethyl-2-butyl, 2,2-dimethyl-butyl, heptyl, octyl, nonyl, decyl, pentadecyl, hexadecyl, heptadecyl, octadecyl, nonadecyl and eicosyl. The substituents $R^1$, $R^2$, $R^3$, $R^4$ and $R^5$ preferably denote, independently of each other, methyl and ethyl, particularly preferably methyl. The substituent $R^5$ preferably denotes straight-chain or branched alkyl having up to 8 carbon atoms of the above-mentioned type, particularly preferably branched alkyl having up to 6 carbon atoms of the abovementioned type.

$C_1$–$C_4$-alkoxy is straight-chain or branched alkyl of the abovementioned type linked via an oxygen atom; correspondingly, alkoxy is taken to mean having up to 10 C atoms. The substituents $R^1$, $R^2$, $R^3$, $R^4$ and $R^6$ preferably denote, independently of each other, $C_1$–$C_2$-alkoxy, particularly preferably methoxy. The substituent $R^5$ preferably denotes straight-chain or branched alkoxy having up to 8 carbon atoms, particularly preferably straight-chain or branched alkoxy having up to 6 carbon atoms.

$C_3$–$C_{10}$-cycloalkyl denotes saturated, unsubstituted or substituted, preferably 3- to 8-membered, particularly preferably 3- to 6-membered, carbocyclic ring systems, where substituents which may be mentioned are, for example, halogen, preferably fluorine or chlorine, and lower alkyl having 1 to 4 carbon atoms, preferably methyl. In this context, cyclopropyl, 1-methyl-cyclopropyl, 1-fluoro-cyclopropyl, 1-chloro-cyclopropyl, cyclobutyl, 1-methyl-cyclobutyl, heptafluoro-cyclobutyl, cyclopentyl, 1-methyl-cyclopentyl, 2,2-dimethyl-cyclopentyl, cyclohexyl, 1-methyl-cyclohexyl, 4,4-dimethylcyclohexyl, 4-tert-butyl-cyclohexyl and 1-adamantyl may be mentioned in particular.

$C_5$–$C_{10}$-cycloalkenyl denotes monounsaturated or polyunsaturated, non-aromatic, unsubstituted or substituted, preferably 5- to 8-membered, particularly preferably 5- and 6-membered, carbocyclic ring systems, where substituents which may be mentioned are, for example, halogen, preferably fluorine or chlorine, and lower alkyl having 1 to 4 carbon atoms, preferably methyl. 1-, 2- and 3-cyclopentenyl, 1-, 2-, 3- and 4-cyclohexenyl, 2-methyl-2-cyclopentenyl, 3-methyl-3-cyclopentenyl, 2-methyl-2-cyclohexenyl, 2-chloro-2-cyclohexenyl, 1-methyl-4-cyclohexenyl and 1,5-dimethyl-5-cyclohexenyl may be mentioned in particular.

Aryl denotes unsubstituted or substituted phenyl having up to 5, preferably up to 4, particularly preferably up to 3, substituents, which can take up any positions in ortho- meta- or para-position to each other. Preferred substituents are halogen, in particular fluorine or chlorine, $C_1$–$C_4$-alkyl, preferably methyl, halogenoalkyl, preferably trifluoromethyl and difluoromethyl, $C_1$–$C_4$-alkoxy, preferably methoxy and ethoxy, halogenoalkyloxy, preferably trifluoromethoxy and tetrafluoroethoxy and $C_1$–$C_4$-alkoxycarbonyl, preferably methoxycarbonyl and ethoxycarbonyl.

Aryloxy denotes unsubstituted or substituted phenyl, linked via an oxygen atom, having up to 5, preferably up to 4, particularly preferably up to 3, substituents which can take up any positions in ortho-, meta- or paraposition to each other. Preferred substituents are halogen, in particular fluorine or chlorine, $C_1$–$C_4$-alkyl, preferably methyl, halogenoalkyl, preferably trifluoromethyl and difluoromethyl, $C_1$–$C_4$-alkoxy, preferably methoxy and ethoxy, halogenoalkyloxy, preferably trifluoromethoxy and tetrafluoroethoxy and alkoxycarbonyl, preferably methoxycarbonyl and ethoxycarbonyl. Halogen denotes, for example, fluorine, chlorine or bromine, preferably fluorine or chlorine.

The leaving group X represents, for example, halogen, preferably fluorine, chlorine or bromine, particularly preferably chlorine, the radical O-$R^5$ or the radical O-CO-$R^5$, in which $R^5$ has the abovementioned meaning. Moreover, in principle, all leaving groups X are suitable which ensure a sufficient activation of the radical CO-$R^5$ in accordance with an acylation, for example alkoxy. Carrying out the process according to the invention may be described with reference to the following example:

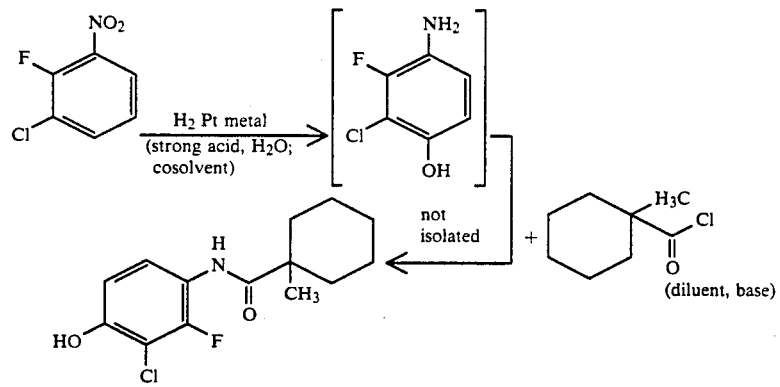

Suitable cosolvents which may optionally be used in accordance with the present invention are in principle all organic, water-miscible solvents which are stable under the reaction conditions used and which do not negatively influence the catalytic hydrogenation. Such cosolvents are, for example, lower alcohols and polyhydric alcohols having 1 to 4 C atoms, such as methanol, ethanol, n- and i-propanol, n-, i-, sec- and tert-butanol, ethylene glycol, 1,2- and 1,3-propanediol, 1,2-, 1,3-, 1,4- and 2,4-butanediol and 1,2,3-propanetriol. Further examples are water-soluble ethers of the polyhydric alcohols mentioned such as glycol monomethyl ether and glycol dimethyl ether, glycol monoethyl ether and glycol diethyl ether. Examples of further cosolvents which may be used according to the invention are water-soluble cyclic ethers, such as tetrahydrofuran and dioxan, water-miscible ketones, such as acetone and methyl ethyl ketone, water-soluble carboxylic amides, in particular those alkylated twice on the nitrogen atom, such as N,N-dimethylacetamide, N,N-dimethylformamide and the corresponding ethylated lower carboxylic amides, and lower aliphatic carboxylic acids having 1 to 4 C atoms, such as formic acid, acetic acid or propionic acid. The abovementioned lower alcohols ethylene glycol and its monomethyl and dimethyl ethers of the abovementioned type and dioxan may be preferably mentioned. Methanol, ethanol, ethylene glycol, glycol monomethyl ether and glycol dimethyl ether and dioxan may be particularly preferably mentioned. The abovementioned cosolvents can be used either individually or alternatively as a mixture of a plurality thereof.

The amount of the organic, water-miscible solvent which may be used is 0.01 to 3 times, preferably 0.03 to 2 times, particularly preferably 0. 05 to 1 times the amount by weight of the aromatic nitro compound.

Strong inorganic or organic acids are useful for the aqueous acidic reaction medium, for example, sulphuric acid, phosphoric acid, nitric acid, hydrochloric acid, perchloric acid, methanesulphonic acid, toluenesulphonic acid, perfluoromethanesulphonic acid and others known to those skilled in the art. Sulphuric acid or one of the sulphonic acids mentioned are preferably used; sulphuric acid is particularly preferably used.

The amount of the strong acids is 0.4 to 10 equivalents, preferably 0.5 to 2 equivalents, particularly preferably 0.5 to 1.2 equivalents, based on 1 mol of the aromatic nitro compound.

The amount of water for the aqueous acidic reaction medium is 2 to 40 times, preferably 3 to 30 times, particularly preferably 4 to 20 times the amount by weight of the aromatic nitro compound.

The process according to the invention is carried out at a temperature of 50° to 160° C., preferably 60° to 140° C,. particularly preferably 70° to 120° C.

Elevated pressure is employed for the catalytic hydrogenation in the context of the process according to the invention, for which purpose a pressure reactor of any desired type, such as is known to those skilled in the art, is employed. Obviously, such a reactor is acid-resistant under the reaction conditions to be established according to the invention. A pressure of 2 bar up to 50 bar may be mentioned as elevated pressure. At this elevated pressure, the hydrogen partial vapour pressure accounts for 0.1 to 50 bar, preferably 0.5 to 30 bar, particularly preferably 1 to 20 bar, and therefore can thus also go to make up the overall pressure of up to 50 bar. The difference between the hydrogen partial vapour pressure and the overall pressure is generally the inherent pressure of the reaction system, that is the vapour pressure of the water and of the organic, water-miscible solvent to be added. The vapour pressure of the nitro compound additionally contributes. Furthermore, after filling the pressure reactor with the substances to be reacted and the reaction medium, flushing with inert gas, such as nitrogen, noble gas etc., is necessary for the problem-free course of a catalytic hydrogenation. A residue of the inert flushing gas remaining in the pressure reactor after it has been closed also contributes to the overall pressure. A procedure is generally followed for this such that the closed pressure reactor is brought to the desired reaction temperature before the hydrogen partial vapour pressure is established by forcing in hydrogen. Hydrogen is then added for as long as it is taken up by the reaction mixture.

Catalysts which are useful for the process according to the invention are noble metals selected from the platinum group, in particular platinum and/or palladium. Similarly, compounds of the platinum metals, for example platinum compounds and/or palladium compounds, can be used. These compounds are then reduced by the hydrogenating hydrogen to form platinum metal active in hydrogenation. The platinum metal or a compound of the platinum metal can be used with or without a support. Supports can, for example, be silica gel, aluminum oxide, zeolites, molecular sieves, charcoal or other supports known to those skilled in the art, preferably charcoal. When a support is used with the catalyst, the metal coating is 0.05 to 8% by weight, preferably 0.1 to 6% by weight, particularly preferably 0.25 to 5% by weight of the total catalyst. The catalyst, with or without support, is used in such an amount that 0.001 to 0.3% by weight, preferably 0.005 to 0.1% by weight, particularly preferably 0.01 to 0.1% by weight of the platinum metal is present, based on the nitro compound to be reacted.

The entire reaction mixture is intensively stirred during the hydrogen uptake. For this purpose the pressure reactor is equipped with an agitator or a lifting device or is designed as a shaking autoclave.

It is characteristic of the process according to the invention that the catalysts used, after termination of the reduction step or after termination of the entire reaction sequence, preferably after termination of the reduction step, can be recovered in an unchanged active or almost unchanged active form.

The isolation of the catalyst after termination of the reduction step or after the entire reaction sequence is achieved by filtration, decanting or centrifugation from the remaining reaction mixture.

If the removal and recovery of the catalyst is carried out immediately after the reduction step, it can, possibly, be advantageous to wholly or partly remove from the reaction mixture any cosolvent possibly used in the course of carrying out this reduction step. This can be carried out at elevated or reduced pressure or at atmospheric pressure by distillation, preferably by distillation at reduced pressure.

Diluents which are useful for carrying out the 2nd reaction step of the process according to the invention are organic solvents which are inert under the reaction conditions. These include, in particular, aliphatic, alicyclic or aromatic, unhalogenated or halogenated hydrocarbons such as benzine, benzene, toluene, xylene, chlorobenzene, petroleum ether, hexane, cyclohexane, dichloromethane, chloroform, carbon tetrachloride, ethers such as diethyl ether, dioxan, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate or sulphoxides such as dimethyl sulphoxide.

The 2nd reaction step of the process according to the reaction can thus be carried out in a two-phase system, such as water/toluene or water/dichloromethane, in the absence or presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyl-dimethyl-ammonium ethyl sulphate, dimethyl-$C_{12}$/$C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxy-ethoxy)-ethyl]-amine.

Basic auxiliaries which are useful for carrying out the 2nd reaction step of the process according to the invention are all conventionally usable inorganic and organic bases. Alkali metal hydroxides or alkaline earth metal hydroxides, alkali metal carbonates or hydrogen carbonates or alkaline earth metal carbonates or hydrogen carbonates, such as potassium hydroxide, calcium hydroxide, sodium hydroxide, potassium carbonate, calcium carbonate, sodium carbonate or sodium hydrogen carbonate or tertiary amines such as triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a relatively wide range when the 2nd reaction step of the process according to the invention is carried out. Generally, temperatures between $-30°$ C. and $+150°$ C. are employed, preferably temperatures between $-20°$ C. and 120° C., particularly preferably temperatures from $-10°$ C. to $+100°$ C.

The 2nd part-step of the process according to the invention is generally carried out at atmospheric pressure. However, it is also possible to carry it out at reduced or elevated pressure.

To carry out the 2nd part-step of the novel process according to the invention, 0.5 to 2.0 mol of the acylation reagent (for example the acid chloride), preferably 0.8 to 1.4 mol, and 2 to 5 mol of the basic auxiliary (for example sodium hydroxide), preferably 3 to 4 mol per mol of the nitroaromatic compound used as starting material are generally used.

The reaction procedure, work-up and isolation of the reaction products are carried out by generally conventional methods (see also the preparation examples).

The process according to the invention is carried out using a nitrobenzene or a 1-nitro-naphthalene which can be substituted in accordance with formula (II). It is preferably carried out using a nitrobenzene which can be substituted in accordance with formula (II).

Important aromatic nitro compounds as starting materials for the process according to the invention are: nitrobenzene, 2-nitrotoluene, 3-nitrotoluene, 2-chloronitrobenzene, 3-chloro-nitrobenzene, 2-ethyl-nitrobenzene, 3-ethyl-nitrobenzene, 2-acetyl-nitrobenzene, 3-acetyl-nitrobenzene, 2-nitrobenzoic acid and esters, 3-nitrobenzoic acid and esters, 2-fluoro-nitrobenzene, 3-fluoro-nitrobenzene, 2,3-dichloro-nitrobenzene, 2,3-difluoro-nitrobenzene, 2-chloro-3-fluoro-nitrobenzene, 2-fluoro-3-chloro-nitrobenzene, 1-nitronaphthalene, 2-chloro-3-methyl-nitrobenzene, 2-methyl-3-chloro-nitrobenzene.

From such nitro compounds, according to the invention, are formed the corresponding p-aminophenols, preferably those of the benzene series, which are then acylated according to the invention.

The following aromatic nitro compounds of the benzene series may preferably be mentioned from which are formed the corresponding p-aminophenols of the benzene series which are then to be acylated: 2,3-dichloro-nitrobenzene, 3-nitrobenzoic acid, 2-fluoro-nitrobenzene, 3-fluoro-nitrobenzene, 2-nitrotoluene, 3-nitrotoluene, 2-chloro-nitrobenzene, 3-chloro-nitrobenzene, 2-nitrobenzoic acid, 2-chloro-3-fluoro-nitrobenzene, 2-fluoro-3-chloro-nitro-benzene, 2-chloro-3-methyl-nitrobenzene and 2-methyl-3-chloro-nitrobenzene.

EXAMPLE 1

96 g (0.5 mol) of 2,3-dichloronitrobenzene, 20 ml of dimethoxyethane (DME), 400 ml of water, 60 g of 98% strength (0.6 mol) sulphuric acid and 1 g of platinum catalyst (5% on activated charcoal) were introduced into a 1.3 l enamel autoclave and heated with vigorous stirring to 105° C.

10 bar of hydrogen were then applied and the mixture was hydrogenated to constant pressure.

200 ml of water were added to the reaction mixture and this was filtered hot.

150 ml of DME/water mixture were distilled off on a rotary evaporator and the resulting suspension was transferred into a four-necked flask equipped with stirrer, reflux condenser, dropping funnel and pH electrode.

The mixture was adjusted to pH 5.5 using 20% strength sodium hydroxide solution, 250 ml of toluene were added and the mixture was heated to 50° C.

30.5 g (0.19 mol) of 1-methylcyclohexanecarbonyl chloride were added dropwise in the course of 30 min, the mixture was stirred for a further 10 min and then adjusted to pH 4.5 using 20% sodium hydroxide solution.

14.5 g (0.09 mol) of acyl chloride were then added dropwise four times successively in the course of 15 min, the mixture was stirred for a further 5 min and the pH was adjusted to 5.5 using 20% strength sodium hydroxide solution.

After the last addition of sodium hydroxide solution, the mixture was stirred for a further 1 hour, adjusted to pH 2.5 using concentrated HCl, heated to 80° C., adjusted to pH 1.5 using concentrated HCl and stirred for a further 1 hour.

The mixture was cooled to 0° C. in the course of 2 hours, filtered using suction and washed at room temperature using 2×100 ml of water.

After drying, 2',3'-dichloro-4'-hydroxy-1'-methylcyclohexanecarboxanilide was obtained in 70% yield (based on 2,3-dichloronitrobenzene used).

EXAMPLE 2

The reaction sequence of Example 1 was repeated, 22.9 g and 4×10.9 g of pivaloyl chloride being used instead of 1-methylcyclohexanecarbonyl chloride. 2',3'-dichloro-4'-hydroxypivalanilide was obtained in 72% yield (based on 2,3-dichloronitrobenzene used).

EXAMPLE 3

42.9 g (0.276 mol) of 2-chloro-3-nitrotoluene, 80 ml of dimethoxyethane, 400 ml of $H_2O$, 30 g of $H_2SO_4$ (98% strength=0.3 mol) and 2 g of 5% Pt/C were placed in a 1.3 l enamel autoclave and heated with vigorous stirring to 100° C.

10 bar of hydrogen were then applied and the mixture was hydrogenated to constant pressure.

The reaction mixture was filtered hot, concentrated on a rotary evaporator to 300 ml and transferred into a four-necked flask equipped with stirrer, reflux condenser, dropping funnel and pH electrode.

The mixture was adjusted to pH 5.5 using 20% strength sodium hydroxide solution, 100 ml of toluene were added and the mixture was heated to 50° C.

15.8 g (0.1 mol) of 1-methylcyclohexanecarbonyl chloride were added dropwise in the course of 20 min, the mixture was stirred for a further 5 min and again adjusted to pH 5.5 using 20% strength sodium hydroxide solution.

7.2 g (0.045 mol) of carbonyl chloride were then added dropwise in each of four steps in the course of 10 min, the mixture was stirred for a further 3 min and adjusted to pH 5.5 using 20% strength sodium hydroxide solution.

After the last addition of sodium hydroxide solution, the mixture was stirred for a further 30 min, adjusted to pH 2.5 using concentrated HCl, heated to 80° C., adjusted to pH 1.5 using concentrated HCl and stirred for a further 30 min.

The mixture was cooled to 0° C. in the course of 2 hours, filtered using suction and washed at room temperature using 3×50 ml of water.

After drying, 77% 2'-chloro-4'-hydroxy-1,3'-dimethylcyclohexanecarboxanilide were obtained.

What is claimed is:

1. A process for the preparation of a N-acylated p-aminophenol of the general formula

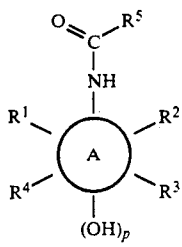

in which
A represents a benzene or naphthalene nucleus,
p indicates the p position to the amino group,
$R^1$, $R^2$, $R^3$ and $R^4$, independently of each other, denote hydrogen, $C_1$-$C_4$-alkyl, $C_1$-$C_4$-alkoxy, halogen or the group CO—$R^6$ in which $R^6$ represents hydrogen, $C_1$-$C_4$-alkyl, $C_1$-$C_4$-alkoxy, hydroxyl or unsubstituted or substituted aryl, and
$R^5$ denotes $C_1$-$C_{20}$-alkyl, $C_3$-$C_{10}$-cycloalkyl, $C_5$-$C_{10}$-cycloalkenyl, $C_1$-$C_{10}$-alkoxy, unsubstituted or substituted aryloxy or unsubstituted or substituted aryl,
wherein a nitro compound of the general formula

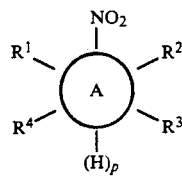

in which
$R^1$ to $R^4$, A and p have the above meanings,
is hydrogenated in an aqueous acidic reaction medium in which the amount of water is 2 to 40 times the amount by weight of the aromatic nitro compound, and in the absence or presence of a water-miscible organic solvent with the aid of a catalyst selected from the group consisting of the platinum metals in accordance with a Bamberger reaction at a temperature of 50°-160° C. and a hydrogen partial pressure of 0.1-50 bar and the resulting reaction mixture is reacted with the compound of the formula

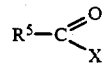

where
$R^5$ has the above meaning and
X represents a leaving group,
in an amount of 0.5-2 per mol of the nitro compound used, at a temperature of −30° C. to +150° C. and in the absence or presence of a basic auxiliary or another acid acceptor and in the absence or presence of a diluent.

2. The process of claim 1, wherein the amount of water is 3 to 30 times the amount by weight of the aromatic nitro compound.

3. The process of claim 2, wherein the amount of water is 4 to 20 times the amount by weight of the aromatic nitro compound.

4. The process of claim 1, which is carried out at 70°-140° C.

5. The process of claim 4, which is carried out at 90°-120° C.

6. The process of claim 1, which is carried out at 0.5-30 bar.

7. The process of claim 6, which is carried out at 1-20 bar.

8. The process of claim 1, wherein the radicals $R^1$, $R^2$, $R^3$, $R^4$ and $R^6$, independently of each other, denote hydrogen, methyl, ethyl, methoxy or ethoxy, where the radicals $R^1$ to $R^4$ can additionally denote fluorine, chlorine or bromine or the group CO—$R^6$ and the radical $R^6$ can additionally denote hydroxyl or unsubstituted or substituted phenyl.

9. The process of claim 1, wherein the radical $R^5$ denotes $C_1$-$C_8$-alkyl, $C_3$-$C_6$-cycloalkyl, $C_5$-$C_8$-cycloalkenyl, $C_2$-$C_8$-alkoxy, unsubstituted or substituted phenoxy or unsubstituted or substituted phenyl.

10. The process of claim 1, wherein the leaving group X has the meaning fluorine, chlorine, bromine, O—$R^5$ or O—CO—$R^5$, where $R^5$ has the range of meanings given in claim 1.

11. The process of claim 10, wherein the leaving group X has the meaning chlorine, O—$R^5$ or O—CO—$R^5$, where $R^5$ has the range of meanings given in claim 1.

12. The process of claim 1, wherein the organic, water-miscible solvent(s) used is(are) one or more selected from the group consisting of the lower alcohols and polyhydric alcohols having 1 to 4 C atoms, the monomethyl, dimethyl, monoethyl and diethyl ethers of such polyhydric alcohols, the water-soluble cyclic ethers, the water-soluble ketones, the water-soluble lower carboxylic amides and the lower aliphatic carboxylic acids having 1 to 4 C atoms, where the amount of the organic, water-miscible solvent is 0.01 to 3 times the amount by weight of the aromatic nitro compound.

13. The process of claim 12, wherein the organic, water-miscible solvent(s) used is(are) one or more selected from the group consisting of the lower alcohols, ethylene glycol and its monomethyl, dimethyl, monoethyl and diethyl ethers and dioxane.

14. The process of claim 13, wherein the organic, water-miscible solvent(s) used is(are) one or more selected from the group consisting of the methanol, ethanol, ethylene glycol, glycol monomethyl ether and glycol dimethyl ether and dioxane.

15. The process of claim 1, wherein, as the acid, sulphuric acid or an organic sulphonic acid is used in an amount of 0.4 to 10 equivalents per mol of the aromatic nitro compound.

16. The process of claim 15, wherein the acid is used in an amount of 0.5-2 equivalents per mol of the aromatic nitro compound.

17. The process of claim 1, wherein when the 2nd reaction step of the process according to the invention is carried out, the diluents used are inert organic solvents from the group of aliphatic, alicyclic or aromatic, unhalogenated or halogenated hydrocarbons, ethers or ethylene glycol dimethyl ether or ethylene glycol diethyl ether, ketones, nitriles, amides, esters or sulphoxides.

18. The process of claim 1, wherein the 2nd reaction step of the process according to the invention is carried out, a basic auxiliary is used from the group of alkali metal hydroxides or alkaline earth metal hydroxides, alkali metal carbonates or hydrogen carbonates or alkaline earth carbonates or hydrogen carbonates or tertiary amines.

19. The process of claim 18, wherein the basic auxiliary is one or more from the group of potassium hydroxide, calcium, hydroxide, sodium hydroxide, potassium carbonate, calcium carbonate, sodium carbonate or sodium hydrogen carbonate, triethylamine, N,N-dimethyl-aniline, pyridine, N,N-dimethylaminopyridine, diazabicyclooctane (DABCO), diazabicyclononene (DBN) or diazabicycloundecene (DBU).

20. The process of claim 1, wherein the nitro compound used is one selected from the group consisting of nitrobenzene, 2-nitrotoluene, 3-nitrotoluene, 2-chloronitrobenzene, 3-chloro-nitrobenzene, 2-ethyl-nitrobenzene, 3-ethyl-nitrobenzene, 2-acetylnitrobenzene, 3-acetyl-nitrobenzene, 2-nitrobenzoic acid and esters, 3-nitrobenzoic acid and esters, 2-fluoronitrobenzene, 3-fluoro-nitrobenzene, 2,3-dichloro-nitrobenzene, 2,3-difluoro-nitrobenzene, 2-chloro-3-fluoro-nitrobenzene, 2-fluoro-3-chloro-nitrobenzene, 1-nitronaphthalene, 2-chloro-3-methyl-nitrobenzene, 2-methyl-3-chloro-nitrobenzene.

* * * * *

UNITED STATES PATENT AND TRADEMARK OFFICE
CERTIFICATE OF CORRECTION

PATENT NO. : 5,302,742
DATED : April 12, 1994
INVENTOR(S) : Heinz Landscheidt, et al.

It is certified that error appears in the above-identified patent and that said Letters Patent hereby corrected as shown below:

| | |
|---|---|
| Col. 10, Line 12 | After "0.5-2" insert --mol-- |
| Col. 11, Line 19 | After "wherein" insert --when-- |
| Col. 12, Line 1 | After "earth" insert --metal |

Signed and Sealed this

Eighth Day of February, 2000

Attest:

Q. TODD DICKINSON

*Attesting Officer*     *Commissioner of Patents and Trademarks*